US006673079B1

(12) United States Patent
Kane

(10) Patent No.: US 6,673,079 B1
(45) Date of Patent: Jan. 6, 2004

(54) DEVICE FOR LENGTHENING AND RESHAPING BONE BY DISTRACTION OSTEOGENESIS

(75) Inventor: Alex A. Kane, St. Louis, MO (US)

(73) Assignee: Washington University, St. Louis, MO (US)

( * ) Notice: Subject to any disclaimer, the term of this patent is extended or adjusted under 35 U.S.C. 154(b) by 490 days.

(21) Appl. No.: 09/640,140

(22) Filed: Aug. 16, 2000

Related U.S. Application Data
(60) Provisional application No. 60/148,762, filed on Aug. 16, 1999.

(51) Int. Cl.[7] .................................................. A61F 2/38
(52) U.S. Cl. ............................ 606/105; 606/60; 606/63
(58) Field of Search ........................... 606/105, 63, 90, 606/60, 62, 64, 65, 67, 68, 69, 72, 73, 74; 433/7

(56) References Cited

U.S. PATENT DOCUMENTS

| | | | |
|---|---|---|---|
| 5,622,493 A | 4/1997 | Razdolsky et al. | 433/7 |
| 5,626,581 A | 5/1997 | Staehlin et al. | 606/63 |
| 5,704,938 A | 1/1998 | Staehlin et al. | 606/62 |
| 5,769,850 A | 6/1998 | Chin | 606/53 |
| 5,807,382 A | 9/1998 | Chin | 606/53 |
| 5,810,812 A | 9/1998 | Chin | 606/53 |
| 5,829,971 A | 11/1998 | Razdolsky et al. | 433/7 |
| 5,846,245 A | 12/1998 | McCarthy et al. | 606/105 |
| 5,873,715 A | 2/1999 | Liou | 433/18 |
| 5,902,304 A | 5/1999 | Walker et al. | 606/71 |
| 5,976,142 A | 11/1999 | Chin | 606/73 |
| 6,019,769 A | 2/2000 | McCarthy et al. | 606/105 |
| 6,033,412 A | 3/2000 | Losken et al. | 606/105 |
| 6,099,536 A * | 8/2000 | Petillo | 606/142 |
| 6,245,075 B1 * | 6/2001 | Betz et al. | 606/105 |

FOREIGN PATENT DOCUMENTS

DE  196 45 392 C 1  11/1996

OTHER PUBLICATIONS

Caleffi E., Bocchi A., Toschi S., Montacchini G., Papadia F.; Annals of the MBC; vol. 3–n'3 *Tissue Expansion In The Treatment of Burn Scars*; Sep. 1990; 4 pages; www.medbc.com./annals/review/vol 3/num 3/text/vol3n3p177.htm.
American Society of Plastic Surgeons; *Plastic Surgery Information Service, The Surgery, Tissue Expansion*; 1992; 7 pages; http://www.plasticsurgery.org/surgery/tisexp.htm.
PMT Corp.; *Tissue Expanders, Accuspan and Integra*; Sep. 1997; 2 pages; http://www.pmtcorp.com/texpander.htm.
Hamilton Company; *OEM Components, Precision Syringe Pumps*; 1998; 2 pages; http://www.hamiltoncomp.com/product/oem/pumps.html.
Advanced Liquid Handling, Inc.; *MBP2000 Syringe Pump*; No Date; 2 pages http://www.alhinc.com/mbp2k.html.
Univentor LTD Products Specifications; *SPECIFICATIONS, The Univentor 400 Anaesthesia Unit*; No Date; 9 pages; http://www.univentor.com/specificationspage.html.
Children's Medical Center of Dallas; *Distraction Osteogenesis*; No Date; 2 pages; http://www.kidsplastsurg.com/distraction.html.

* cited by examiner

*Primary Examiner*—Cary E. O'Connor
*Assistant Examiner*—Candice C. Melson
(74) *Attorney, Agent, or Firm*—Senniger, Powers, Leavitt & Roedel

(57) ABSTRACT

An implantable bone distractor is created which grips both sides of a cut bone by the use of screws and plates, then applies an expansion force between the cut bone edges. This force is applied in order to encourage bone growth in the gap formed between the cut bone edges as they are distracted apart. This force is applied with hydraulic jacks, which are actuated using tubes passing through the skin, allowing the controlled application of force between the cut bone edges from external to the body. The distraction may occur in three-dimensions, with each bone segment being distracted within its own plane. The distraction may be further improved by providing substantially continuous distraction of the bone segments over time, allowing for substantially continuous bone growth.

14 Claims, 8 Drawing Sheets

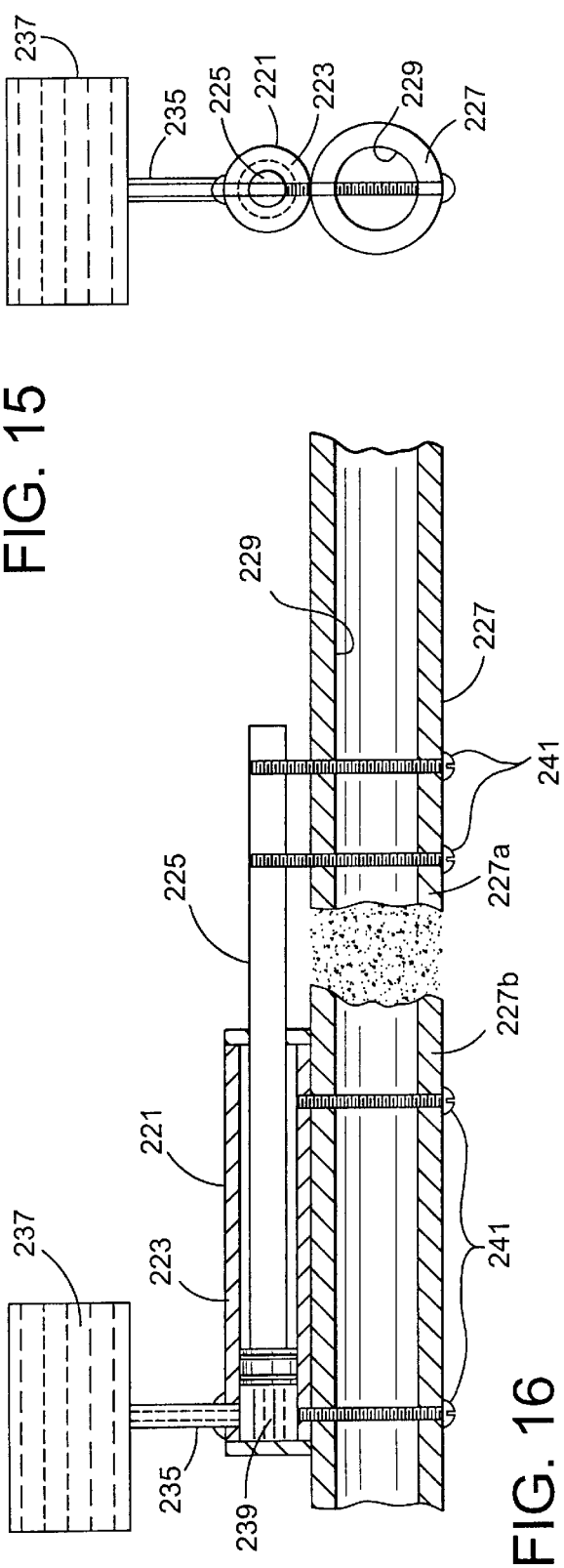
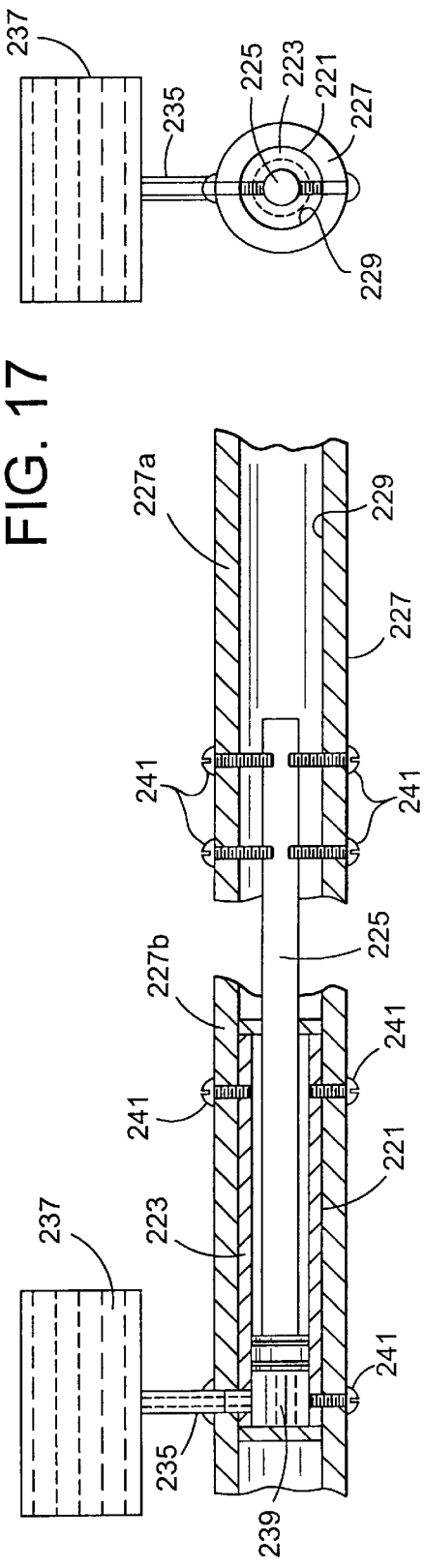

DEVICE FOR LENGTHENING AND RESHAPING BONE BY DISTRACTION OSTEOGENESIS

This application is the complete application based on U.S. Provisional application Serial No. 60/148,762, filed Aug. 16, 1999.

BACKGROUND OF THE INVENTION

This invention relates generally to devices and methods for living tissue reshaping and, more particularly, to achieving three-dimensional bone lengthening and reshaping by distraction osteogenesis.

In many instances where the bone of a patient is malformed or deficient, correction can frequently be made by distraction osteogenesis. Bone defects of this type may stem from either congenital or acquired bone defects. Commonly these defects are birth defects, requiring treatment on infants. Examples of such defects include, for example, one leg, or arm, may be shorter than the other, due to bone deformity, or perhaps where the jaw or other bone structure is malformed or deficient, treatment is required to reshape such bone structure, trying to provide the appearance of normality, besides viable structure and functionality to the affected skeletal structure. Distraction osteogenesis utilizes the natural regenerative capability of the living tissue in bone to augment and shape the bone. Generally speaking, the bone is broken into two pieces and slowly separated, stimulating growth of bone in the gap to achieve a desired shape.

For example, treatment for patients with shortened leg structure is known. Where a patient has a thigh bone (femur) which is shorter on one side compared with another, the surgeon cut the bone in two at the site where new bone was desired. An external jacking mechanism, commonly referred to as a circumferential metal scaffolding, is attached to the bone sections above and below the bone cut by way of bone screws. Conventionally, the jacking mechanism includes a series of, for example, jack screws, or regular screws that can be tightened, to provide for lengthening of the bone structure, to achieve its normal length. By tightening the jack screws a certain number of turns per day, the separation between sections of bone infinitesimally increases, sometimes only approximately 1 mm (0.04 inches), per day, or the like, to gradually lengthen the bone. Additional bone structure, whether calcium deposit or other bone structure, grows in the intermediate gap, filling the gap and lengthening the bone, sometimes to significant lengths. Lengthening a bone by inches is common by these earlier methods.

The natural phenomenon of new bone creation across a gap that is slowly widened by the application of a distraction force has been well described, and has become known as the principle of "distraction osteogenesis," and is a common technique used by both orthopedic and craniofacial surgeons to lengthen or alter the shape of bone. Prior art devices have applied the distraction force largely through a screw drive mechanism, or other metal mechanical drive mechanism that imparts force to widen the gap by turning the screw a fixed amount per unit time.

One drawback of such a prior art method is scarring of the patient's skin caused by the movement of the external jacking device with respect to the skin as the device extends the gap between the bone sections. Another drawback of transmitting tissue shaping forces through long bolts is the increase in device deflection as the device is placed more remote to the bone structure. This deflection results in less precise movement of the bone structure. Furthermore, prior art jacking devices external to the patient are often uncomfortable for the patient due to their bulk and weight. A few prior art devices disclose a distraction osteogenesis device incorporating a fully implantable jacking mechanism. There is a need, therefore, for a distraction osteogenesis device capable of providing linear, uniplanar, and multiplanar distraction osteogenesis with a fully implantable jacking device. Moreover, there is a need for a device that distracts tissue segments accurately and continuously in three-dimensions while reducing scarring and hiding itself from view.

SUMMARY OF THE INVENTION

Among the several objects of this invention may be noted the provision of a distraction device which is implantable within a body of a living thing for three-dimensional reshaping of living tissue; the provision of a distraction device which allows for substantially continuous distraction of living tissue for reshaping and regeneration of living tissue; the provision of a distraction device which is very small for implantation within small areas within the body of a small living thing, such as a child; the provision of a distraction device which reduces scarring of the skin by ensuring that portions of the device passing through the skin pass at a point where no displacement of the device occurs; the provision of a distraction device which moves external portions of the device to inconspicuous areas of the living thing's body to hide scars better; and the provision of a distraction device which uses a hydraulic mechanism for fluid and forceful movement of regenerative living tissue.

Generally, a distraction device is disclosed for controlled movement of at least two sections of regenerative living tissue, such as bone, within the body of a living thing relative to each other in three-dimensions to foster reshaping the living tissue. The device comprises a first jack unit having a first extendable member adapted for attachment to one of the sections of living tissue. A second jack unit having a second extendable member is adapted for connection to the other of the sections of living tissue. An actuator is adapted for actuating extension of the extendable members to move the sections of living tissue apart for controlled regeneration of tissue between the sections. A joint interconnecting the first and second jack units is adapted to permit orientation of the first and second jack units relative to each other in three-dimensions. The jack units and joint are sized and shaped for implantation within the body for three-dimensional living tissue reshaping with movement of the device confined entirely within the body.

In another aspect of the present invention, a tissue expansion mechanism for expanding living tissue, such as bone, to foster reshaping of living tissue within the body of a living thing, is disclosed. The mechanism comprises an expansion device adapted for engagement with living tissue to foster reshaping the living tissue. The expansion device is capable of exerting a force with respect to the living tissue so that engagement of the expansion device with the living tissue induces the living tissue to expand according to the influence of the expansion device. The mechanism further comprises an automated control device adapted for connection to the expansion device to substantially continuously and automatically actuate the expansion device to foster reshaping of the living tissue.

In still another aspect of the present invention, a distraction hydraulic jack is disclosed for controlled movement of at least two sections of regenerative living tissue, such as bone, within the body of a living thing relative to each other to foster reshaping the living tissue. The hydraulic jack comprises a cylinder adapted for attachment to one of the sections of living tissue. A piston is partially received within said cylinder for movement of the piston with respect to the cylinder. The sliding, sealing inter-engagement of the piston and the cylinder form a sealed cavity within the cylinder. The portion of the piston not received within the cylinder is adapted for attachment to the other of the sections of living tissue. Both the cylinder and piston are sized and shaped for implantation within the body for living tissue reshaping with movement of the device confined entirely within the body. A hydraulic fluid source mounts externally to the body in fluid connection with the cavity for transmitting hydraulic fluid into the cavity. The fluid is incompressible such that additional fluid entering the cavity pushes the piston outward with respect to the cylinder such that the partially received portion extends outward from the end of the cylinder, thereby transmitting a force along the axis of the hydraulic jack so that the two sections move apart a specific distance.

In yet another aspect of the present invention, a method is disclosed for performing controlled movement of at least two sections of regenerative living tissue, such as bone, within the body of a living thing relative to each other in three-dimensions to foster reshaping the living tissue. The method comprises the steps of surgically exposing a portion of regenerative living tissue within the body and severing the regenerative living tissue into at least two sections. The method further entails attaching a distraction device to said at least two sections. The distraction device further comprises a hydraulic actuation system including a hydraulic fluid transport tube extending from the hydraulic actuation system to the distraction device for configuring the distraction device in three-dimensions for achieving three-dimensional distraction. The method comprises the additional step of implanting the distraction device entirely within the body of the patient and allow a free end of the fluid transport tube to extend from the body for connection to the hydraulic actuation system. The method comprises yet another step of regulating a flow of hydraulic fluid into the free end of the fluid transport tube from outside the body to control the hydraulic actuation system for controlled movement of the distraction device and the sections relative to one another at a specific orientation and distance to foster regenerative tissue growth between the sections.

Other objects and features will be in part apparent and in part pointed out hereinafter.

BRIEF DESCRIPTION OF THE DRAWINGS

FIG. 14 is a schematic, side section of a linear, extramedullary distraction hydraulic jack of the present invention as applied to a bone;

FIG. 15 is an end view of the distraction hydraulic jack and bone of FIG. 14;

FIG. 16 is a schematic, side section of an intramedullary distraction hydraulic jack implanted within a bone; and FIG. 17 is an end view of the distraction hydraulic jack and bone of FIG. 16.

Corresponding reference characters indicate corresponding parts throughout the several views of the drawings.

DETAILED DESCRIPTION OF THE PREFERRED EMBODIMENT

Figure 1:
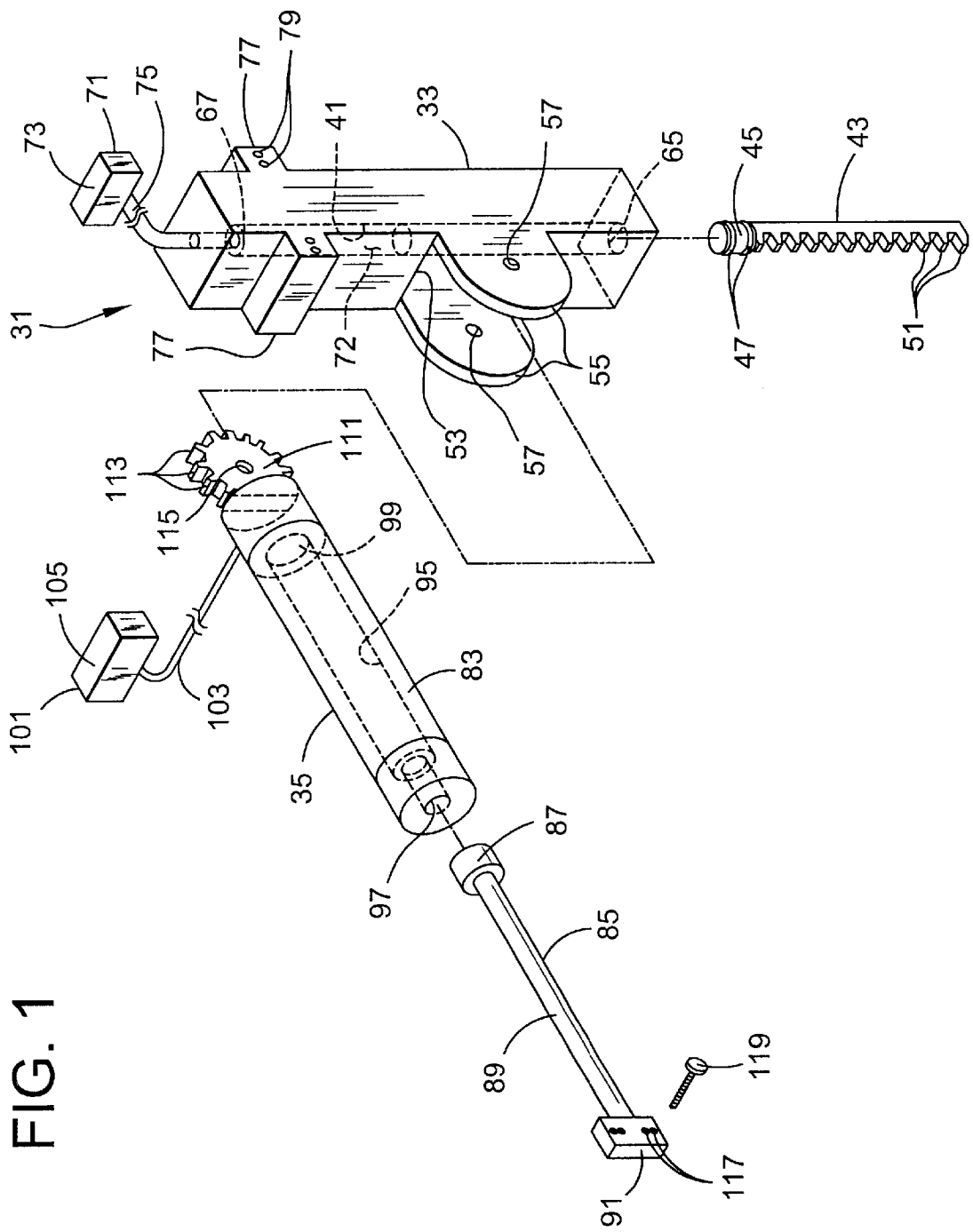
FIG. 1 is a schematic, exploded perspective view of a jack unit of the present invention.

Referring now to the drawings and specifically to FIG. 1, a jack unit of the present invention is generally indicated at 31. This embodiment of the invention may be used in situ, directly in communication and contact with an affected bone structure, to achieve a displacement of the bone for distraction osteogenesis. The jack unit 31 comprises an angular control jack 33 and a linear control jack 35. The angular control jack 33 includes a cavity 41 sized and shaped for receiving a linearly movable rack 43. Both the cavity 41 and rack 43 are cylindrical in shape. The rack 43 includes a head end 45 having two annular seals 47 for creating a tight seal within the cavity 41. Opposite the head end 45, the rack 43 includes a plurality of teeth 51 spaced at regular intervals. The angular control jack 33 further includes an opening 53, exposing the teeth 51 of the rack 43 inside the angular control jack. Two tabs 55 flank the opening 53 and extend perpendicular to the opening. Both tabs 55 further include a hole 57 for receiving a pin 59, as discussed in more detail below, and shown in FIGS. 2–4. The cavity 41 further includes an open end 65 and a substantially closed end 67. The rack 43 is inserted head end first into the open end 65 of the cavity 41. The closed end 67 of the cavity 41 is in communication with an angular actuator 71, so that the space within the cavity between the head end 45 of the rack 43 and the closed end 67 of the cavity forms a chamber 72. In the preferred embodiment, the angular actuator 71 is a hydraulic reservoir 73 connectible to the cavity 41 via a flexible tube 75. The hydraulic reservoir 73 preferably contains a saline solution or another incompressible and nonimmunogenic fluid. A valve (not shown) within the flexible tube 75 is capable of blocking fluid flow for maintaining fluid within the chamber 72 or releasing fluid from the chamber. The angular control jack 33 further comprises mounting flanges 77 for attaching the angular control jack 33 to bone or other tissue (not shown). The mounting flanges 77 extend from opposite sides of the angular control jack 33 and include two fastener holes 79 for receiving bone screws or other attachment devices (not shown). The bone screws allow the mounting flanges 77 to attach to some bone or other tissue sought to be displaced with the jack unit 31. The fastener holes 79 in the flanges 77 may be of any number, size and arrangement while remaining within the scope of the present invention. Moreover, other attachment structure is also contemplated as within the scope of the present invention, including but not limited to, clamps, adhesives and other mechanical or chemical fasteners.

Figure 2:
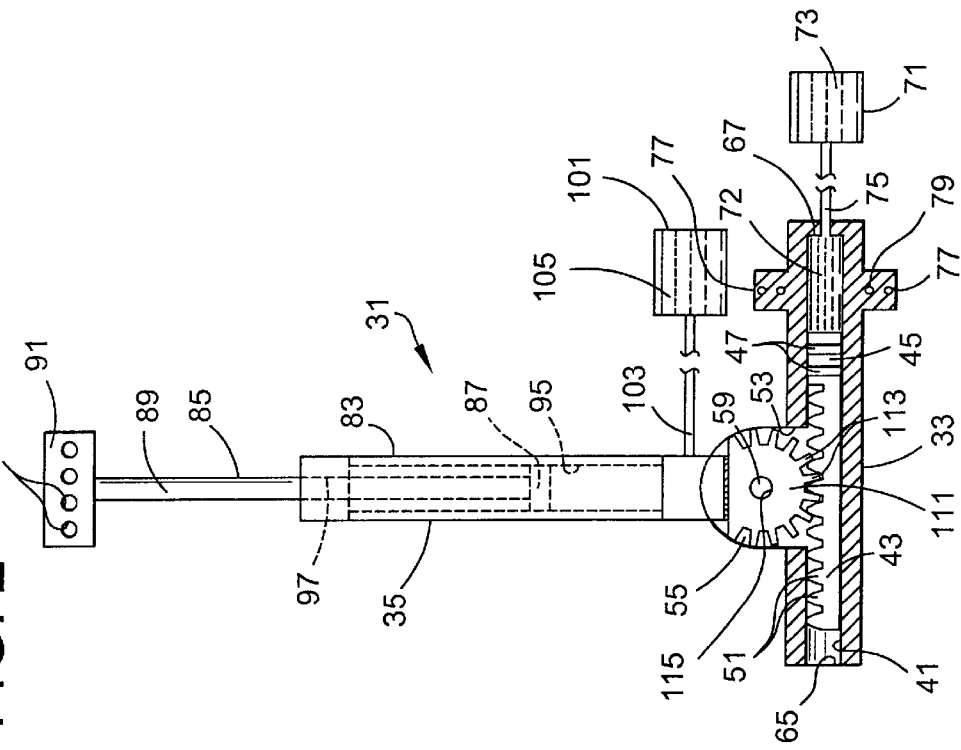
FIG. 2 is an elevation and partial section of the jack unit of FIG. 1 with a linear control jack arranged perpendicular to an angular control jack.

The linear control jack 35 comprises a cylinder 83 and an extendable member 85. The extendable member 85 includes a piston 87, a rod 89 and a mounting plate 91. The piston 87 and rod 89 are both cylindrical in shape and arranged coaxially. The cylinder 83 includes a cylindrical cavity 95 for receiving the piston 87 and rod 89. The cylindrical cavity 95 includes an open end 97 and a closed end 99. The piston 87 includes a sealing means, such as an o-ring (not shown), for creating a sliding, sealing fit between the cylindrical cavity 95 and the piston. The rod 89 passes through the open end 97 of the cavity 95. The closed end 99 of the cylindrical cavity 95 is in communication with a linear actuator 101, substantially identical to the angular actuator 71 as set forth above, including both a flexible tube 103, a hydraulic reservoir 105 and a valve (not shown). A pinion gear 111, or pinion, is fixed to the proximal end of the cylinder 83. The pinion 111 includes a plurality of teeth 113 disposed about the perimeter of the pinion sized and shaped for engagement with the teeth 51 of the rack 43. The pinion 111 includes a centrally located hole 115 sized and shaped for receiving the pin 59 (FIG. 2). The pin 59 passes through the tabs 55 of the angular control jack 33 and the pinion 111 of the linear control jack 35, so that the linear control jack is selectively pivotable with respect to the angular control jack. Moreover, the teeth 113 of the pinion 111 mesh with the rack 43 so that linear movement of the rack induces the linear control jack 35 to pivot about the axis of the pin 59. The mounting plate 91 mounts on a distal end of the rod 89 and includes a plurality of fastener holes 117 for receiving bone screws 119 for attaching the mounting plate to some bone sought to be displaced with the jack unit 31. The fastener holes 117 in the mounting plate 91 may be of any number, size and arrangement while remaining within the scope of the present invention. Moreover, other attachment structure is also contemplated as within the scope of the present invention, including but not limited to, clamps, adhesives and other mechanical or chemical fasteners. The device may easily be modified to be used expressly to expand soft tissues, utilizing the same principle of force application by hydraulic jacks.

The angular control jack 33, linear control jack 35 and flexible tubes 75 must be formed from a nonimmunogenic material that is fully implantable within the body of a living thing, such as a human being or other animal. The jacks 33, 35 may be formed from, but are not limited to, titanium and surgical stainless steel, while the flexible tubes may be appropriately formed from reenforced silastic or other non-immunogenic tubing. A reenforced tube is preferable to an elastic tube because any expansion of the tube 75 during use will result in less hydraulic fluid passing into the chamber and a corresponding reduction in movement of the jacks 33, 35.

Figure 3:
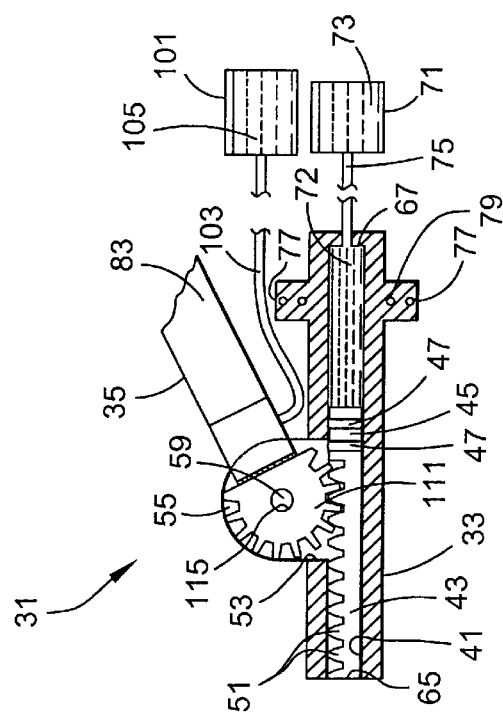
FIG. 3 is an enlarged fragmentary elevation and partial section of the jack unit of FIG. 2.
Figure 4:
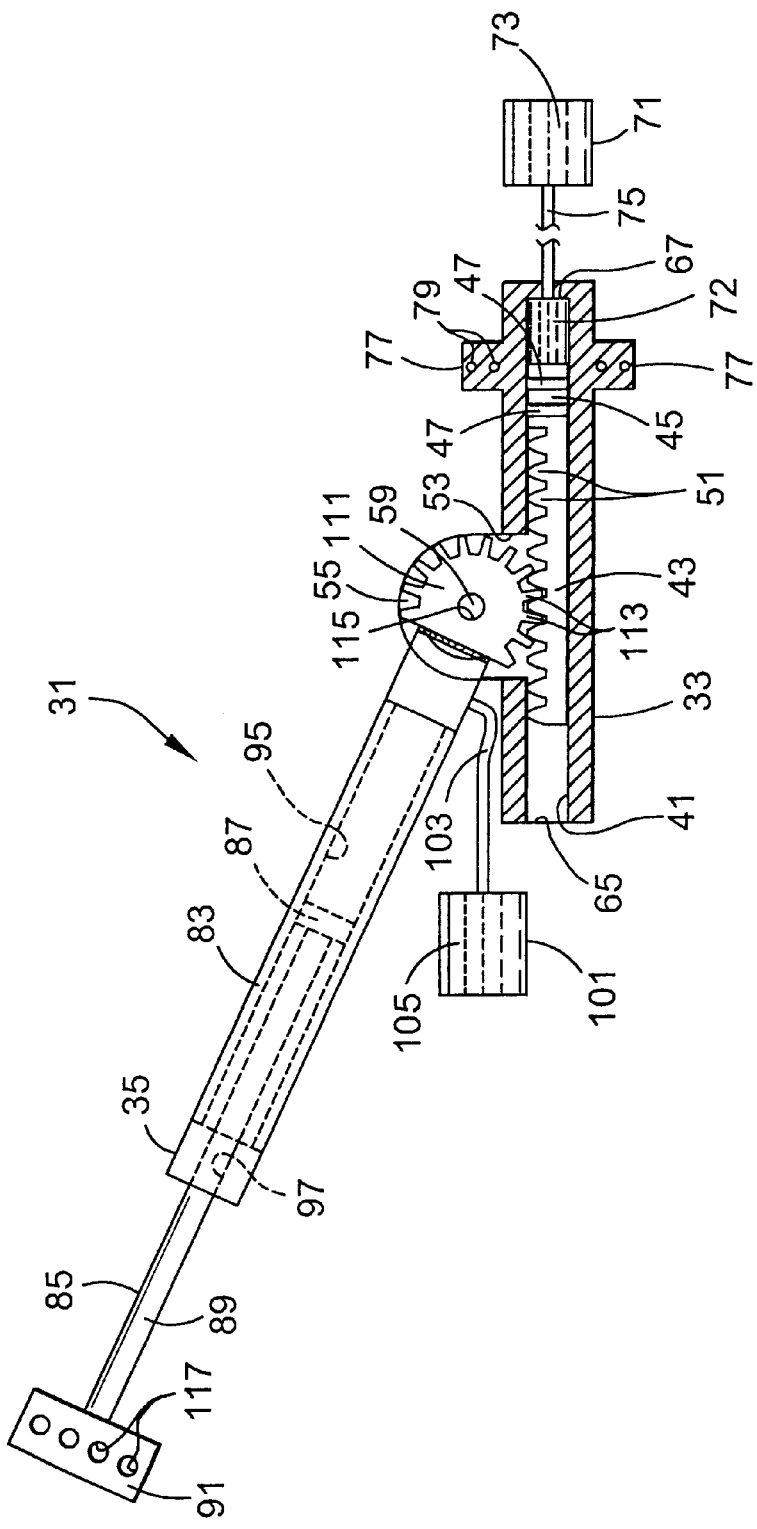
FIG. 4 is an elevation and partial section of the jack unit of FIG. 1 with the linear control jack arranged at an angle to the angular control jack.

In operation, the actuators 71, 101 control movements of the jack unit 31 for pivoting and extension of the extendable member 85 to move two sections of living tissue apart for controlled regeneration of tissue between the sections. The angular control jack 33 is adapted for movement of the extendable member 85 within a specified plane, and the linear control jack 35 is adapted for movement of the extendable member along a line within the plane. Referring to FIG. 2, the angular control jack 33 and linear control jack 35 are perpendicular. The chamber 72 is partially filled with saline so that the rack 43 and pinion 111 are arranged at the midpoints of their potential travel. Should more saline be introduced into the chamber 72, as shown in FIG. 3, the rack 43 moves toward the open end 65 of the cavity 41, inducing pivoting motion of the pinion 111 and linear control jack 35 about the pin 59. Should saline be drawn from the chamber 72, as shown in FIG. 4, the rack 43 moves toward the closed end 67 of the cavity 41, inducing pivoting motion of the pinion 111 and linear control jack 35 in the opposite direction about the pin 59. Introduction of more or less saline into the cylindrical cavity 95 of the linear control jack 35 will induce motion of the extendable member 85 outward and inward with respect to the proximal end of the cylinder 83, respectively. Thus, the combined movement of hydraulic fluid, such as saline, within the actuators 71, 101 allows the jack unit 31 to control movement of two bone portions in any orientation within the plane of the jack unit. This provides added control over the final shape of the new bone, allowing the reshaped bone to grow in more than a single direction. As the bone sections move apart, changing the angle between the angular control jack 33 and the linear control jack 35 create a curved portion of new bone, with a uniplanar device. Thus, in clinical circumstances where only uniplanar distraction is necessary, the angular control jack 33 is rigidly attached to one end of the cut bone via bone screws passing through fastener holes 79 in the mounting flanges 77 and the other end of cut bone is attached by bone screws 119 to the mounting plate 91 mounted on the rod 89. As discussed previously, other attachment structures are also contemplated as within the scope of the present invention.

Other mechanical interconnections between the angular control jack 33 and the linear control jack 35 are contemplated as within the scope of the present invention. For instance, a piston-cylinder linkage attachable to the linear control jack and angular control jack could replace the rack and pinion mechanism. The linkage could extend, increasing the angle between the jacks, or contract, decreasing the angle between the jacks. It is also contemplated that other actuation systems may be readily adapted without departing from the scope of the invention. For example, an electronic actuation system is contemplated in which small electric motors replace piston-cylinder arrangements for articulating the angular control jack 33 and the linear control jack 35 in the same way as the present invention.

Figure 5:
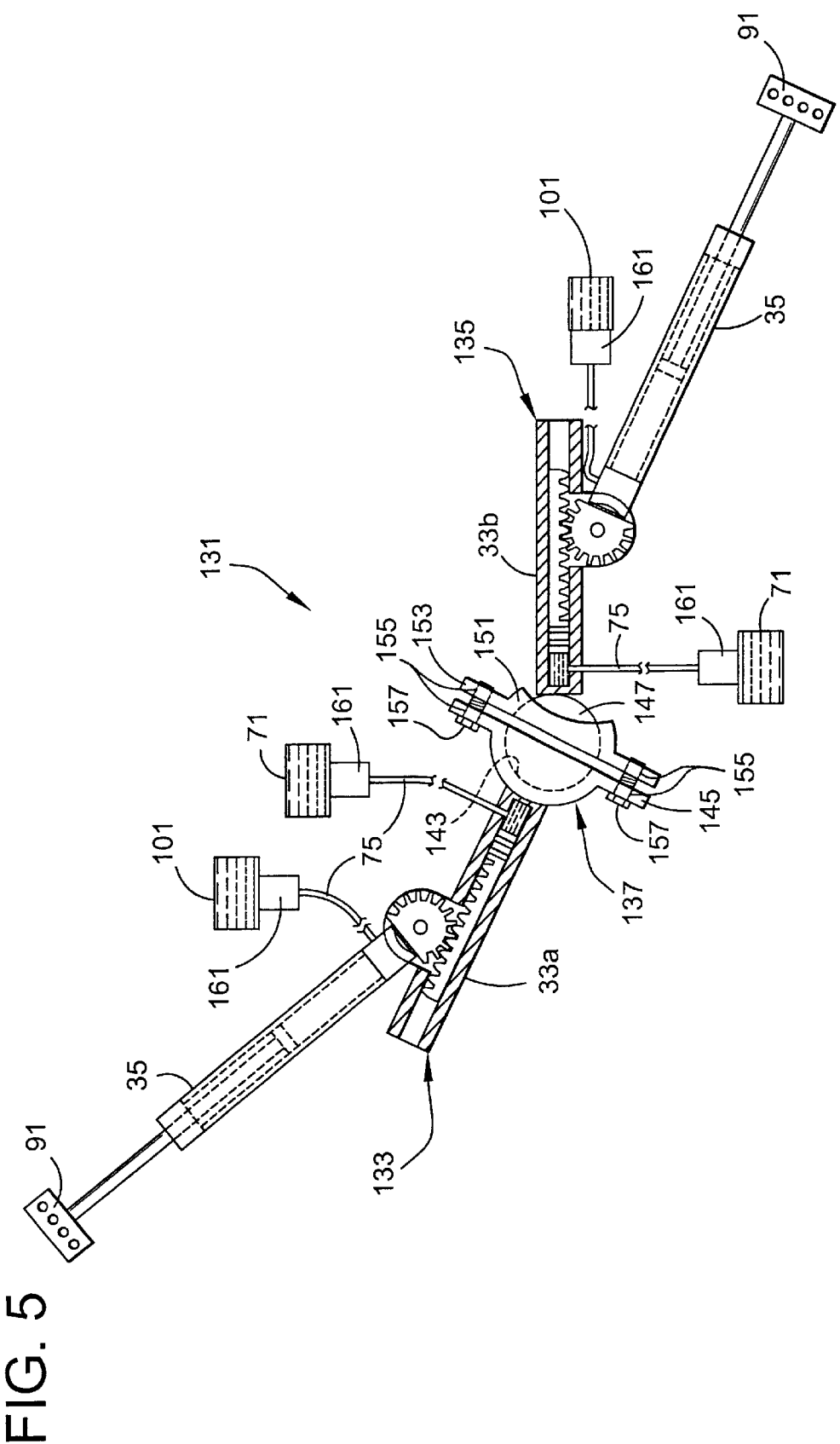
FIG. 5 is a schematic elevation and partial section of a first jack unit and a second jack unit interconnected by a joint.

Referring now to FIGS. 5–10, the preferred embodiment of the present invention is a multiplanar distraction device, generally indicated at 131, wherein a first jack unit, generally indicated at 133, and a second jack unit, generally indicated at 135, both uniplanar, are combined to form a distraction device for bone distraction within two separate planes, and thus in three-dimensions. The jack units 133, 135 are linked via a universal joint, generally indicated at 137, preferably a ball-in-socket design as discussed below, or any other design allowing fixation of the jack units in adjustable orientation in three-dimensions (FIG. 5). For example, the joint may be of the type referred to as a Hooke's universal joint (not shown), slightly modified, wherein the joint is held in a fixed orientation by tightening two pivot bolts about which the joint would normally pivot. The joint 137 is adapted to permit orientation of the first and second jack units 133, 135 relative to each other in three-dimensions. This embodiment allows the cut sections of bone to move apart from each other in a non-planar trajectory. Such a trajectory would be particularly appropriate when used on the non-tubular bones of the craniofacial skeleton, where the desired bone shape has a complex three-dimensional form. As with the single jack unit 31, the jack units 133, 135 and joint 137 are sized and shaped for implantation within the body of a living thing for three-dimensional living tissue reshaping with movement of the device confined entirely within the body.

Figure 9:
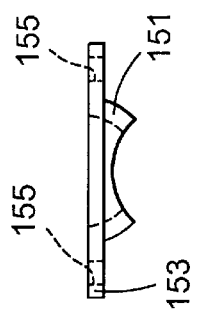
FIG. 9 is an elevation of a joint flange of the joint of FIG. 5.
Figure 10:
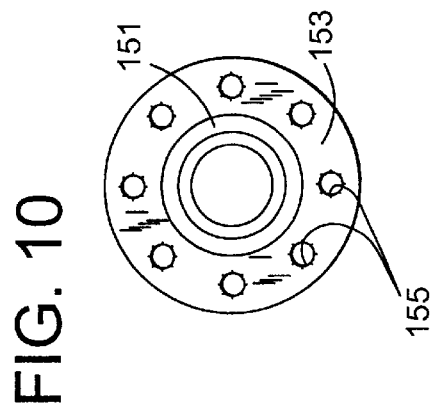
FIG. 10 is a bottom view of the joint flange of FIG. 9.
Figure 8:
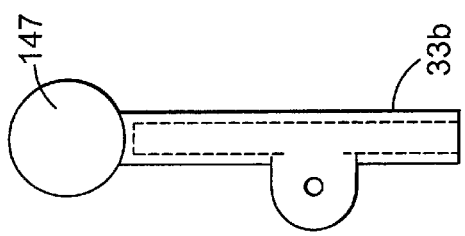
FIG. 8 is an elevation of an angular jack cylinder with a ball portion of the joint of FIG. 5.
Figure 6:
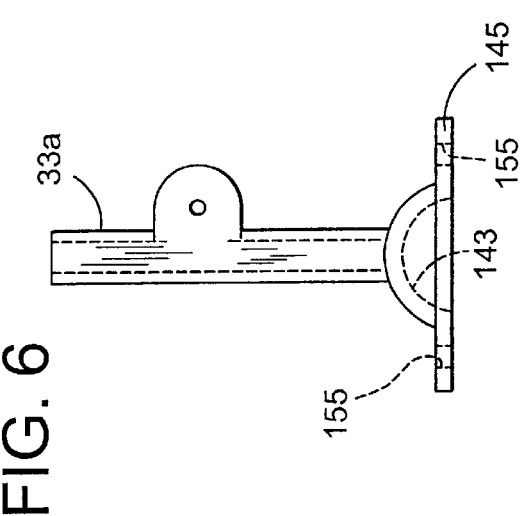
FIG. 6 is an elevation of an angular jack cylinder with a socket portion of the joint of FIG. 5.
Figure 7:
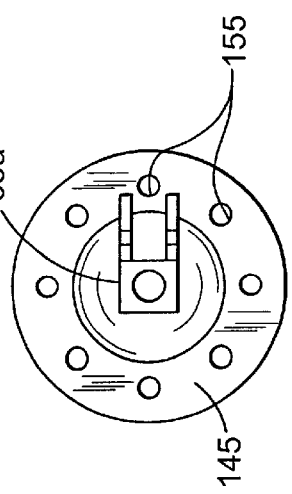
FIG. 7 is a top view of the angular jack cylinder of FIG. 6.

In multiplanar distraction there are two angular control jacks 33a, 33b, neither of which attach directly to bone. The mounting flanges 77 of the previous embodiment, for mounting the annular control jacks directly to bone, may be omitted because the universal joint 137 for interconnecting the first and second jack units 133, 135 is included. The first jack unit 133 comprises an angular control jack 33a having an externally facing socket 143 mounted on a proximal end of the angular control jack (FIGS. 5–7). The socket 143 is hemispherical in shape and includes a first annular flange 145 extending laterally from the socket, the purpose of which will be discussed below. The second jack unit 135 comprises an angular control jack 33b having a spherical ball 147 mounted on a proximal end of the angular control jack (FIGS. 5 and 8). The spherical ball 147 and socket 143 are engageable, so that the ball is in engagement with the entire surface of the socket, irrespective of the orientation of the annular control jacks 33a, 33b with respect to one another. When assembled, a socket plate 151, having a second annular flange 153, is designed for flatwise engagement with the first annular flange 145 and the spherical ball 147 (FIGS. 9–10). The first and second annular flanges 145, 153 each include a plurality of matching bolt holes 155 for receiving bolts 157 to secure the first annular flange 145 to the second annular flange 153 with the spherical ball 147 held within the socket 143. The angular control jacks 33a, 33b may then be oriented in many angular orientations depending upon the desired device application. The first jack unit 133, second jack unit 135, universal joint 137 and flexible tubes 75 must be formed from a nonimmunogenic material that is fully implantable within the body of a living thing, such as a human being or other animal. The jack units 133, 135 and joint 137 may be formed from, but are not limited to, titanium and surgical stainless steel, while the flexible tubes 75 may be appropriately formed from reenforced silastic or other nonimmunogenic tubing. A reenforced tube is preferable to an elastic tube because any expansion of the tube 75 during use will result in less hydraulic fluid passing into the chamber and a corresponding reduction in movement of the jack units 133, 135. Please note that FIGS. 1–10 are included for illustrative purposes only. Proportions are altered to show detail and provide schematic representations of the present invention.

In operation, the multiplanar distraction device 131 is implanted within a patient according to the following process. First, a surgeon performs surgery to access some regenerative living tissue, such as bone. This bone must be in an area of a body accessible to the surgeon where the bone needs to grow or form into a more appropriate size or orientation. The surgeon then severs the bone into at least two sections where bone reshaping is needed. The surgeon selectively orients the jack units 133, 135 in three-dimensions. The universal joint 137 is then locked in the desired orientation by tightening the bolts 157. The mounting plates 91 attach to both osteotomized bone sections with bone screws (not shown). A surgeon skilled in the relevant art will understand how to mount the mounting plate 91 on the bone properly so that the bone can withstand the forces transmitted through the mounting plate. Similarly, the proper orientation of the device will depend upon the desired distraction path and the bone geometry at the attachment point. The surgeon next routes the flexible tubes 75 for transmitting saline away from the device 131 so that they will not interfere with bone growth or movement of the device, routing the ends of the tubes so that they extend from the body for connection to the actuators 71, 101. The surgeon will normally route the tubes 75 so that the free ends of the tubes exit the body at locations hidden from view. These tubes 75 can exit the body at any site that is convenient for the surgeon and the patient. Unobtrusive locations, such as the scalp or in natural skin creases, can camouflage scars, as the tubes 75 pass unnoticed beneath the skin to these sites. This allows application of the devices 131 without great consideration of their positioning with respect to the constraints of accessing a straight screw drive, as with the prior art. Continuing with the procedure, the surgeon closes the surgical area, enclosing the device 131 within the skin of the patient. Finally, the surgeon or another health care professional controls the flow of hydraulic fluid, preferably saline, into the free end of the flexible tubes 75 to control the actuators 71, 101 for controlled movement of the distraction device 131 and the bone sections relative to one another at a specific orientation and distance to foster regenerative bone growth between the sections. The distraction forces applied by the device not only elongate bone, but also naturally expand the adjacent soft tissues. The device may easily be modified to be used expressly to expand soft tissues, utilizing the same principle of force application by hydraulic jacks.

Applying distraction forces externally via tubes 75 that are remote from the site of the cut bone confers several significant advantages that are not available in the prior art. First, it allows the distraction device 131 to be completely submerged inside the body. All communication with the device 131 flows to the site of distraction via the tubes. This differs substantially from much of the prior art, which requires the operator to have physical access to the screw mechanism to rotate the screw regularly, usually at a linear distraction rate of approximately 1 mm (0.04 inches) per day. The requirement for physical access to the screw drive mechanism forces prior art mechanisms to either be external to the body, or if internal, to exit the body through a hole in the skin. For the external devices, the distractors anchor to the bone via pins or screws that must traverse the skin. As these external devices distract the bone, they drag their anchors through the skin along the line of distraction, creating scars that are at least as long as the length of new bone created. These scars can be very disfiguring to patients, especially when on the face. For the internal devices, the distractor is submergible, but the screw drive, or an extension of the screw drive such as a key, exits through a hole in the skin or through a natural orifice such as the oral cavity. These internal devices limit their positioning within the body because the screw turning mechanism must be near a convenient exit hole. Moreover, these metal screw drives are not flexible, in contrast to the flexible tubes of the present invention.

An important benefit of the present invention is the precise planning and execution of a trajectory for the device as it forms new bone or other tissue. This allows the practitioner to completely plan the distraction in three-dimensions as a sequence of infusions and aspirations of the actuators 71, 101 over time. This feature is not available in the prior art. With the present device, it is feasible for the practitioner to take the patient to the operating room, surgically cut a bone into two or more sections, and attach the device. The initial exact three-dimensional position of the device may be recorded with any of several standard three-dimensional imaging techniques, such as a computed tomography scan. A computer can then generate an image of all of the possible final configurations of the device from which the practitioner can select, allowing the practitioner to set a goal orientation of the two pieces of osteotomized bone.

The rate of bone distraction may be controlled substantially continuously and more accurately by a further embodiment of the present invention. Typically, distraction osteogenesis is performed at a rate of about 1 mm (0.04 inches) per day. Practitioners often subdivide this single distraction into multiple smaller distractions taken throughout the day. Continuous distraction of the bone sections very slowly over an entire day may encourage more optimal growth. Thus, a precision pump 161 (shown in FIG. 5 for illustrative purposes) capable of delivering a small charge of fluid, such as saline, many times throughout each hour of a day, attachable to the actuators 71, 101 could deliver a sustained infusion of fluid into the distractor mechanism, causing a substantially continuous distraction at nearly any specified rate. Thus, the distraction process can be nearly automatic with the use of a properly programmed pump 161, requiring little patient or doctor adjustment. The pump 161 may either be implanted within the patient's body or mounted externally to the patient.

Figure 11:
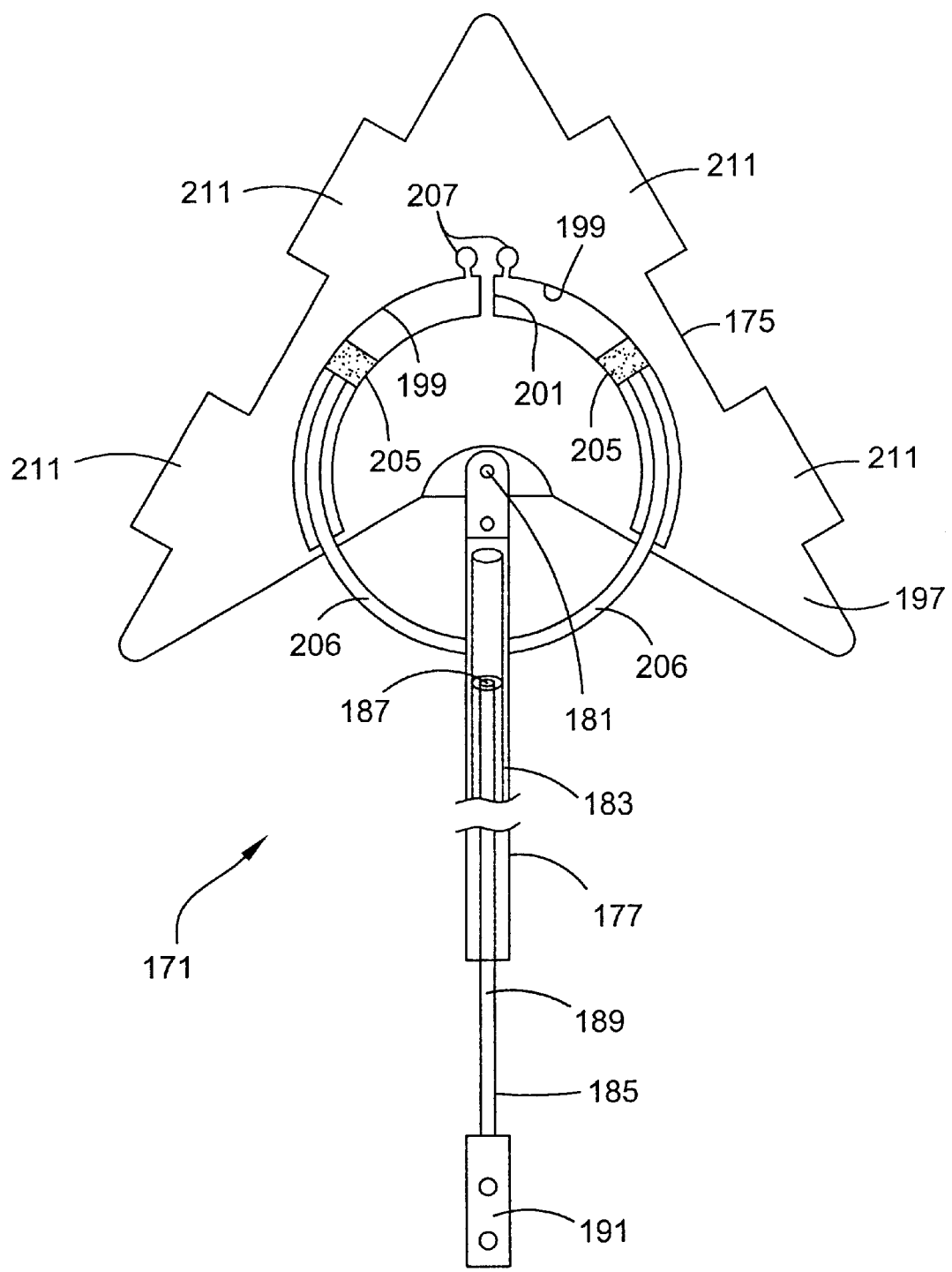
FIG. 11 is a schematic elevation of another embodiment of a jack unit of the present invention with portions removed to show internal construction.

In yet another embodiment of the present invention, a uniplanar jack unit of a slightly different configuration is disclosed in FIGS. 11–15 and generally indicated at 171. Referring now to FIG. 11, a uniplanar jack unit 171 of the present invention is shown. The angular control jack 175 and linear control jack 177 are attached about a pin 181, so that the linear control jack may pivot about the angular control jack. The linear control jack 177 comprises a cylinder 183 and an extendable member 185 as with the previous embodiment. The extendable member 185 comprises a piston 187, a rod 189 and mounting plate 191 as set forth above. The angular control jack 175 comprises a base 197 and two arcuate cylinders 199. These arcuate cylinders 199 lie along the same circular path, passing through the base 197 and spanning a combined 240 degree arc within the base. The cylinders 199 are bisected by a dividing plate 201, which separates the cylinders into two 120 degree cylinders not in fluid communication with one another. Each cylinder 199 is sized and shaped for receiving a piston 205 and arcuate rod 206. Each piston 205 has a sealing means (not shown) for creating a sliding, sealing fit between the piston and arcuate cylinder 199. The free end of each arcuate rod 206 is fixedly attached to the cylinder 183 of the linear control jack 177. Each piston 205 moves opposite the other piston within its respective arcuate cylinder 199 the jack 177 pivots at the pin 181. Each of the two arcuate cylinders 199 has a separate fill valve 207 near the dividing plate 201 (flexible tubes for transporting hydraulic fluid and valves within those tubes are omitted from the figures). The angular control jack 175 controls the pivoting movement of the linear control jack 177 with respect to the base 197. The two arcuate cylinders 199 of the angular control jack 175 complement one another because the same quantity of fluid added to one cylinder is removed from the other. This allows for precisely controlled angular orientation of the linear control jack 177 within the plane of the base 197. Uniplanar angular distraction osteogenesis is accomplished in the plane of the base 197 by attaching the base to one end of the cut bone with screws, while the extendable member 185 of the linear control jack 177 attaches to the other bone section.

Figure 12:
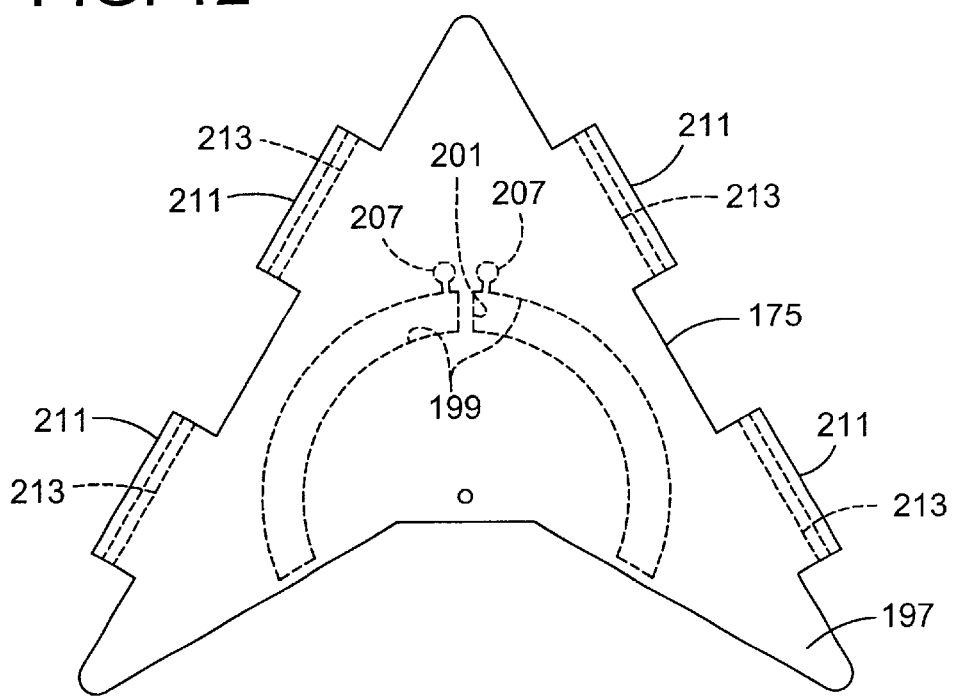
FIG. 12 is an elevation of a top portion of an angular control jack of the jack unit of FIG. 11.
Figure 13:
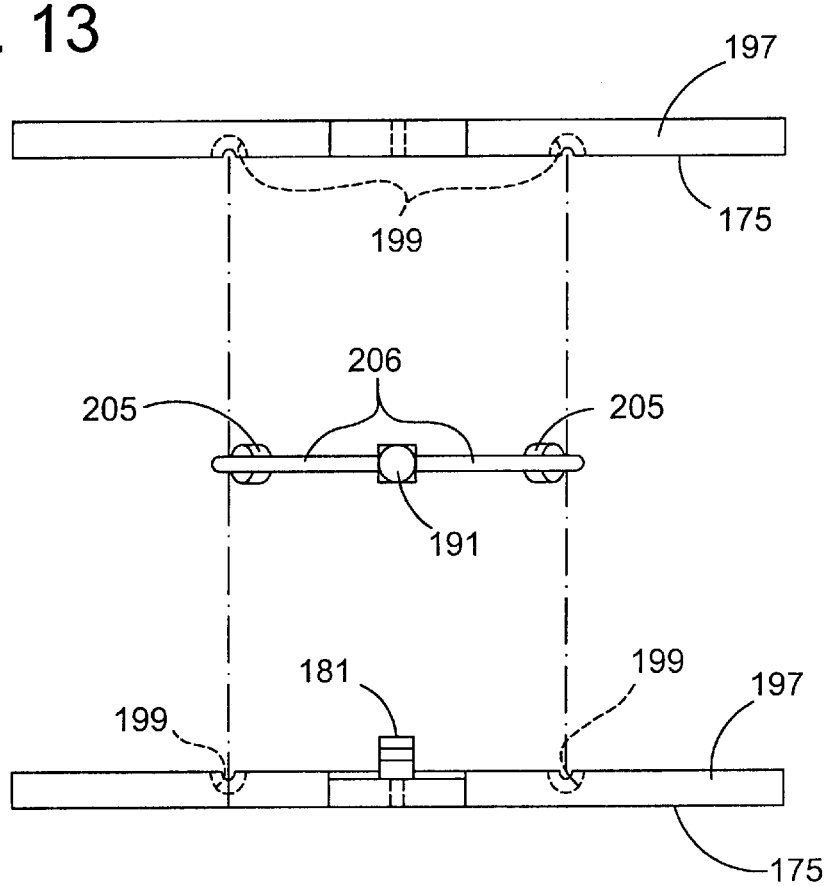
FIG. 13 is an exploded bottom plan view of the top portion of the angular control jack of FIG. 12 illustrating the assembly thereof.

As with the earlier multiplanar embodiment, two uniplanar jack units 171 are linked together in a fixed relationship to form the multiplanar distraction device (not shown). The bases 197 of the two jack units 171 have a series of flanges 211 which extend from the bases at right angles. These flanges 211 each include a star-patterned hole 213 bored through them parallel to the edge of the flange (FIG. 12). To assemble the multiplanar distraction device, the flanges 211 of the two bases 197 are interdigitated so that the star-patterned holes 213 align at whatever planar relationship between the bases 197 is desired by the surgeon. The two bases 197 are then locked in the desired angular relationship by sliding a complementary star-shaped pin through the interdigitated flanges 211 (not shown). For multiplanar distraction, the two bases 197 attach to each other, but not to bone. Distraction proceeds by a sequence of infusions into and aspirations from the two linear control jacks 177 and the two angular control jacks 175, much the same as the previous multiplanar embodiment. This allows the trajectory of new bone growth to be completely controllable in all planes so that the three-dimensional shape of newly formed bone is precisely planned and guided. This trajectory can be completely described as a sequence of control jack movements, and thus can be automated with actuators (not shown). As with the previous embodiments, the components must be formed from a nonimmunogenic material that is fully implantable within the body of a living thing, such as a human being or other animal. Moreover, substantially continuous distraction by a precision pump as described previously is readily applicable to the present embodiment. The distraction forces applied by the device not only elongate bone, but also naturally expand the adjacent soft tissues. The device may easily be modified to be used expressly to expand soft tissues, utilizing the same principle of force application by hydraulic jacks.

Referring now to FIGS. 14–17, another embodiment of the present invention is shown. A linear control jack 221 including a cylinder 223 and an extendable member 225 mounts on the outside surface of a straight bone 227 (FIGS. 14–15) or within the medullary cavity 229 of a straight bone (FIGS. 16–17). The extendable member 225 attaches to one bone section 227a while the cylinder 223 attaches to the other bone section 227b. The bone sections 227a, 227b are actuated as with previous linear control jacks, through a flexible tube 235 and a hydraulic actuator 237 in fluid communication with a chamber 239 located within the cylinder 223 and behind the extendable member 225. The cylinder 223 and extendable member 225 attach to the bone 227 with bone screws 241, or other similar structure, which traverse the cortex of the bone and thread into the metal cylinder 223 and extendable member 225 of the jack 221 so that distraction of the linear control jack is transferred to the bone. Transmitting a force along a linear control jack 221 housed within a straight cylinder 223 applies linear expansion forces between the edges of the cut bone 227, creating a linear trajectory of new bone growth between the cut sections. The linear control jack 221 is actuated and the distraction process is carried out via the pumping of a hydraulic fluid, such as saline, into the chamber 239 of the jack from the external actuator 237. The fluid is carried to the chamber 239 by the flexible tube 235 that passes through the skin and enters the chamber via a valve (not shown). The entry of fluid into the chamber 239 of the jack 221 imparts a distracting force onto the piston of the jack, creating the gap into which new bone forms. A valve (not shown) within the flexible tube 235 is capable of blocking fluid flow for maintaining fluid within the chamber 239 or releasing fluid from the chamber. When the bone 227 reaches the goal length, the linear control jack 221 is kept in place for rigid fixation until the bone has sufficiently healed to the extent necessary to allow the device's removal. As with the previous embodiments, the components must be formed from a nonimmunogenic material that is fully implantable within the body of a living thing, such as a human being or other animal. Moreover, substantially continuous distraction by a precision pump as described previously is readily applicable to the present embodiment.

In view of the above, it will be seen that the several objects of the invention are achieved and other advantageous results attained.

When introducing elements of the present invention or the preferred embodiment(s) thereof, the articles "a", "an", "the" and "said" are intended to mean that there are one or more of the elements. The terms "comprising", "including" and "having" are intended to be inclusive and mean that there may be additional elements other than the listed elements.

As various changes could be made in the above without departing from the scope of the invention, it is intended that all matter contained in the above description and shown in the accompanying drawings shall be interpreted as illustrative and not in a limiting sense.

What is claimed is:

1. A distraction device for controlled movement of at least two sections of regenerative living tissue, such as bone, within the body of a living thing relative to each other to foster reshaping of the living tissue, the device comprising:
    a first jack unit comprising a first linear control jack and a first angular control jack, wherein the first linear control jack has a first extendable member adapted for attachment to one of the sections of living tissue, said first angular control jack being adapted for pivoting movement of the first extendable member within a first plane and said first linear control jack being adapted for movement of the first extendable member along a line within said first plane;
    a second jack unit comprising a second linear control jack, wherein the second linear control jack has a second extendable member adapted for attachment to the other of the sections of living tissue, said second linear control jack being adapted for extension of the second extendable member;
    an actuator for actuating extension of the extendable members and pivoting movement of the first extendable member to move the sections of living tissue apart for controlled regeneration of tissue between the sections; and
    a joint interconnecting the first and second jack units, the joint being adapted to permit orientation of the first and second jack units relative to each other, the jack units and joint being sized and shaped for implantation entirely within the body for living tissue reshaping with movement of the device confined entirely within the body.

2. A distraction device as set forth in claim 1 wherein the actuator further comprises at least one hydraulic reservoir and tubes connectable to the first jack unit and the second jack unit for controlled movement of the first and second extendable members.

3. A distraction device as set forth in claim 2 wherein the actuator further comprises a precision pump for delivering a sustained infusion of hydraulic fluid to the first and second jack units.

4. A distraction device as set forth in claim 1 wherein said second jack unit further comprises a second angular control jack, said second angular control jack being adapted for pivoting movement of the second extendable member within a second plane and said second linear control jack being adapted for movement of the second extendable member along a line within said second plane.

5. A distraction device as set forth in claim 4 wherein said first plane and said second plane are coplanar, thereby defining a uniplanar distraction device.

6. A jack unit for controlled movement of at least two sections of regenerative living tissue, such as bone, within the body of a living thing relative to each other to foster reshaping of the living tissue, said jack unit comprising:
    a linear control jack with an extendable member adapted for attachment to one of the sections of living tissue; and
    an angular control jack pivotably connected to said linear control jack, said angular control jack being adapted for attachment to the other of the sections of living tissue, said angular control jack being adapted for pivoting movement of the extendable member of the linear control jack within a plane, said linear control jack being adapted for movement of the extendable member along a line within said plane, and said linear control jack and angular control jack being sized and shaped for implantation entirely within the body for living tissue reshaping with movement of the linear control jack and the angular control jack confine entirely within the body.

7. A jack unit as set forth in claim 6 wherein the linear control jack is selectively pivotable with respect to the angular control jack.

8. A jack unit as set forth in claim 7 wherein a pinion gear attached to the linear control jack meshes with a movable rack received within a cavity of the angular control jack, such that linear movement of the rack within the cavity induces pivoting movement of the linear control jack.

9. A jack unit as set forth in claim 8 wherein the pinion gear includes a plurality of teeth sized and shaped for engagement with a plurality of teeth of the rack.

10. A jack unit as set forth in claim 8 wherein the space within the cavity between the rack and a closed end of the cavity forms a chamber.

11. A jack unit as set forth in claim 10 wherein the chamber is in communication with a hydraulic reservoir, such that an incompressible fluid may be delivered to the chamber to control movement of the rack, which in turn dictates the angular position of the linear control jack.

12. A distraction device for controlled movement of at least two sections of regenerative living tissue, such as bone, within the body of a living thing relative to each other to foster reshaping of the living tissue, the device comprising:
    an angular control jack adapted for attachment to at least one of said sections of regenerative living tissue, said angular control jack being adapted for pivoting movement of a member in a plane, said member being adapted for attachment to another of said sections of regenerative living tissue, the angular control jack and member being sized and shaped for implantation entirely within the body for living tissue reshaping with movement of the device confined entirely within the body; and
    an actuator for actuating pivoting movement of the member relative to the angular control jack to move the sections of living tissue apart for controlled regeneration of tissue between the sections.

13. A distraction device as set forth in claim 12 wherein said member comprises a linear control jack having a first extendable member, said linear control jack being adapted for movement of the first extendable member along a line within said plane.

14. A distraction device as set forth in claim 13 wherein the actuator further comprises at least one hydraulic reservoir and tubes connectable to the angular control jack and the linear control jack for controlled movement of the distraction device.

* * * * *

UNITED STATES PATENT AND TRADEMARK OFFICE
CERTIFICATE OF CORRECTION

PATENT NO. : 6,673,079 B1
DATED : January 6, 2004
INVENTOR(S) : Kane

It is certified that error appears in the above-identified patent and that said Letters Patent is hereby corrected as shown below:

<u>Title page,</u>
Item [*] Notice, delete the phrase "by 490 days" and insert -- by 245 days --

Signed and Sealed this

Nineteenth Day of April, 2005

JON W. DUDAS
*Director of the United States Patent and Trademark Office*